(12) United States Patent
Kamimura

(10) Patent No.: US 11,484,442 B2
(45) Date of Patent: Nov. 1, 2022

(54) EARMUFFS

(71) Applicant: JVCKENWOOD Corporation, Yokohama (JP)

(72) Inventor: Shinji Kamimura, Yokohama (JP)

(73) Assignee: JVCKENWOOD CORPORATION, Yokohama (JP)

(*) Notice: Subject to any disclaimer, the term of this patent is extended or adjusted under 35 U.S.C. 154(b) by 315 days.

(21) Appl. No.: 16/821,417

(22) Filed: Mar. 17, 2020

(65) Prior Publication Data

US 2020/0297540 A1 Sep. 24, 2020

(30) Foreign Application Priority Data

Mar. 19, 2019 (JP) .............................. JP2019-050743

(51) Int. Cl.
*A42B 1/06* (2021.01)
*A61F 11/14* (2006.01)

(52) U.S. Cl.
CPC .................................... *A61F 11/14* (2013.01)

(58) Field of Classification Search
CPC ....................................................... A61F 11/14
See application file for complete search history.

(56) References Cited

U.S. PATENT DOCUMENTS

| 6,295,366 B1* | 9/2001 | Haller | H04R 5/0335 |
| | | | 379/430 |
| 9,693,129 B2* | 6/2017 | Kamada | H04R 1/1041 |
| 2016/0014522 A1* | 1/2016 | Matsumura | H04R 7/18 |
| | | | 29/896.23 |
| 2017/0064436 A1* | 3/2017 | Tamura | H04R 1/1066 |
| 2019/0069065 A1* | 2/2019 | Brace | H04R 1/1008 |
| 2019/0075382 A1* | 3/2019 | Schrader | H04R 1/2884 |

FOREIGN PATENT DOCUMENTS

| CN | 202979247 U | 6/2013 |
| CN | 105213104 A | 1/2016 |
| JP | 2001087248 A | 4/2001 |
| JP | 2009-505790 A | 2/2009 |
| JP | 2017112446 A | 6/2017 |

OTHER PUBLICATIONS

Office Action dated Aug. 18, 2021 issued in corresponding Chinese Application No. 202010127897.X.
Office Action dated Feb. 28, 2022 for application No. CN202010127897.X with English translation attached.
Office Action dated Jul. 12, 2022, in counterpart Japanese application No. 2019-050742.

* cited by examiner

*Primary Examiner* — Simon King
(74) *Attorney, Agent, or Firm* — Nath, Goldberg & Meyer; Jerald L. Meyer; Stanley N. Protigal

(57) ABSTRACT

Earmuffs each include a body portion, and a circular pad portion attached to the body portion and having a contact surface brought into contact with the head of the user during use. The pad portion is provided with slits connecting the inner circumferential surface and the outer circumferential surface and open on the contact surface, the slits being cut into the pad portion so as to be gradually shifted toward the body portion in the circumferential direction.

5 Claims, 7 Drawing Sheets

EARMUFFS

CROSS REFERENCE TO RELATED APPLICATION

This application is based upon and claims the benefit of priority under 35 U.S.C. § 119 from Japanese Patent Application No. 2019-050743, filed on Mar. 19, 2019, the entire contents of which are incorporated herein by reference.

BACKGROUND

The present disclosure relates to earmuffs.

Japanese Translation of PCT International Application Publication No. 2009-505790 discloses a hearing protective device in the form of earmuffs used to protect user's ears against environmental noise.

SUMMARY

The earmuffs disclosed in the above document are used for cutting off outside noise. The earmuffs also have high sound insulating properties and can be used as a device for cutting off outside noise when the user puts earphones in the outer ears to hear sound playback. The user wears the earmuffs so as to cover the earphones put in the outer ears.

The earmuffs allow the user to satisfactorily hear the sound playback through the earphones insulated against outside noise.

When the earphones are a wired type having a cable connecting the earphones with an external device such as a music player, the cable needs to be led to the outside between pad portions of the earmuffs and the head.

Such a structure may cause gaps between the pad portions and the head to impair the sound insulating properties of the earmuffs, and is thus required to be improved to deal with the problem of hindering the user from hearing the sound of the earphones because of outside noise seeping into the pad portions through the gaps, or the problem of leaking the sound of the earphones out of the earmuffs through the gaps.

An aspect of one or more embodiments provides an earmuff including a body portion, and a circular pad portion attached to the body portion and having a contact surface brought into contact with a head of a user during use. The pad portion is provided with at least one slit connecting an inner circumferential surface and an outer circumferential surface and open on the contact surface, the slit being cut into the pad portion so as to be gradually shifted toward the body portion in a circumferential direction.

DETAILED DESCRIPTION

Earmuffs according to an embodiment of the present disclosure are illustrated below with earmuffs 51 of an example.

Example

Figure 1:
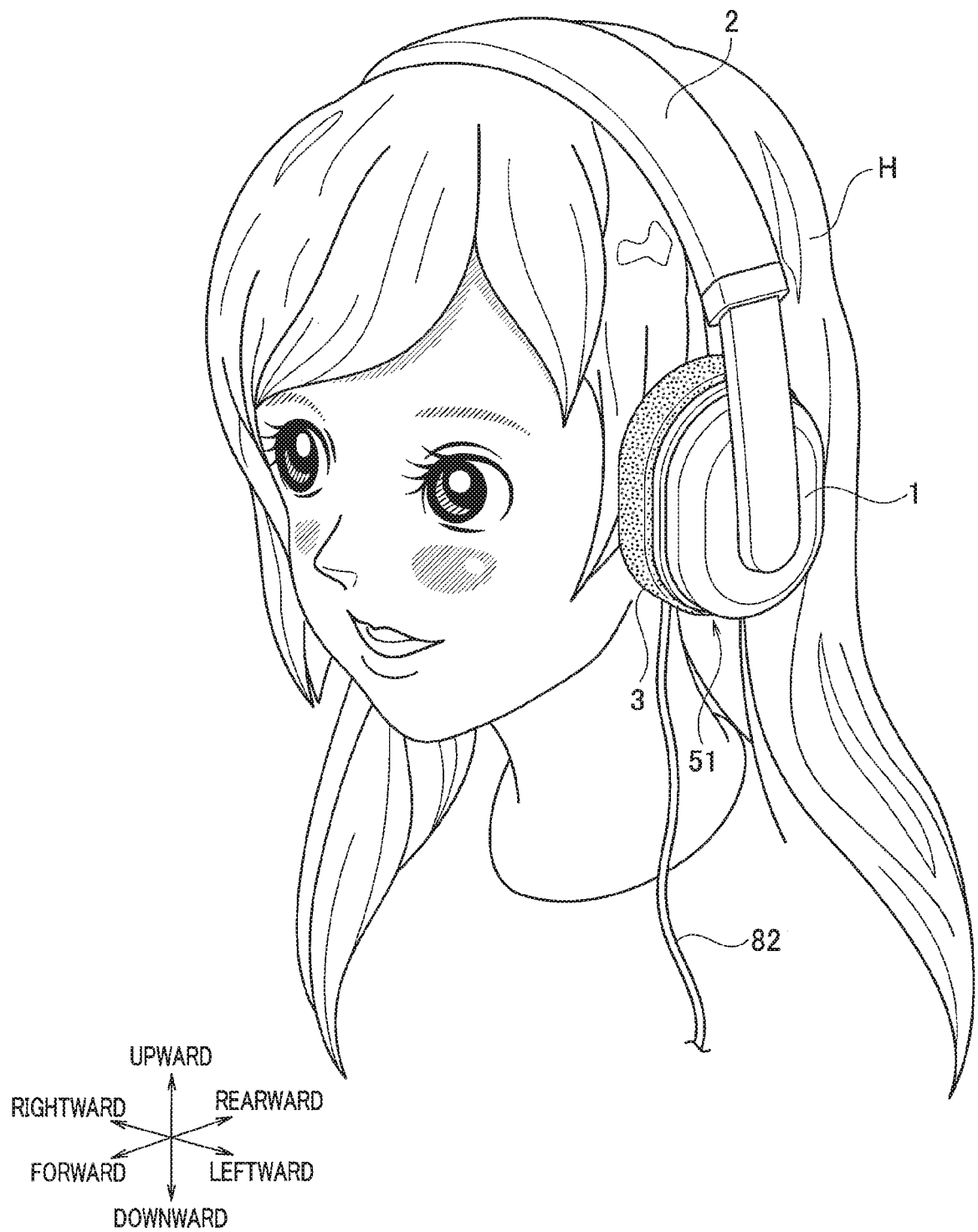
FIG. 1 is a perspective view showing earmuffs 51 as an example of earmuffs according to an embodiment while being put on the head H with a wired earphone fitted in the outer ear.
Figure 5:
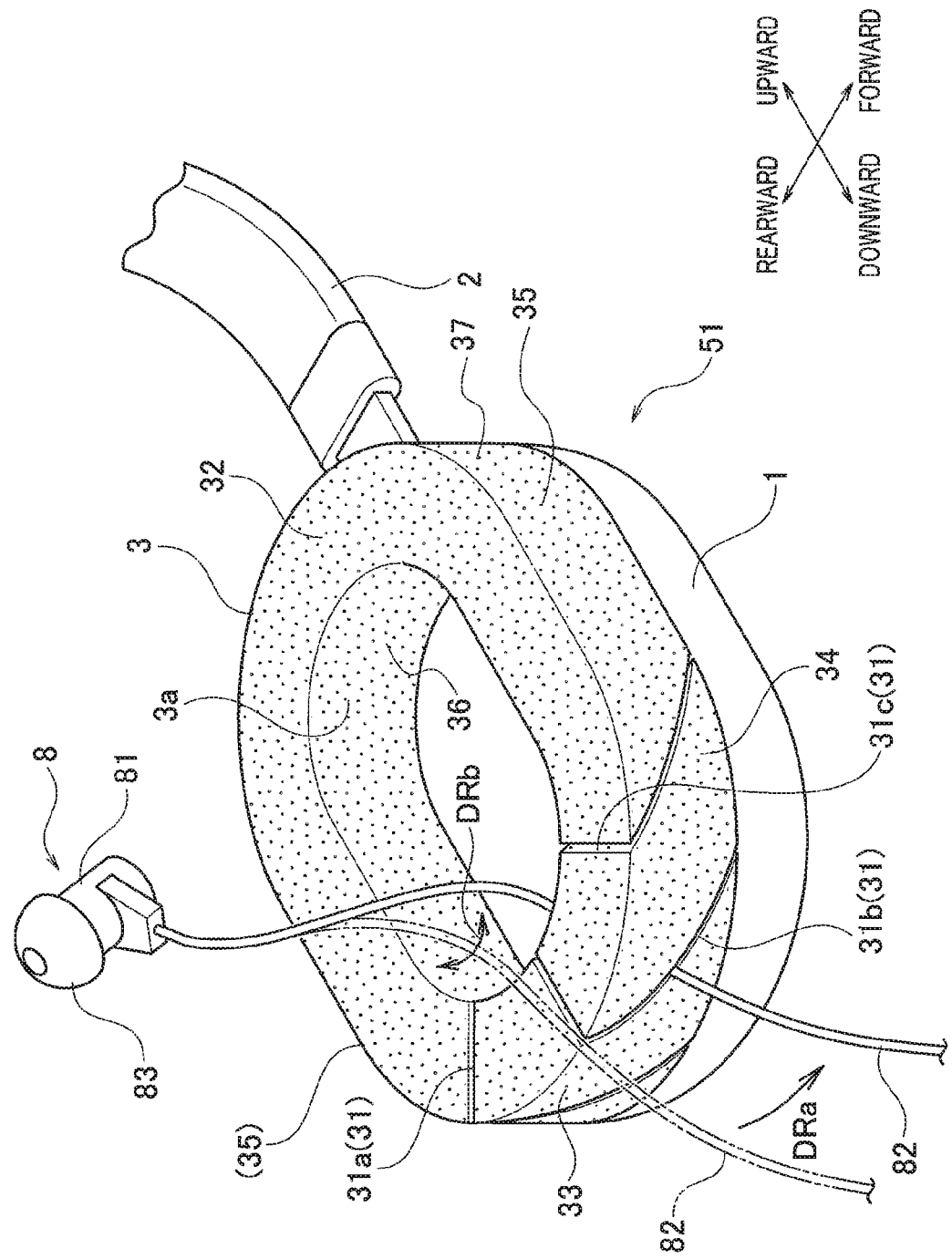
FIG. 5 is a perspective view illustrating a process of inserting a cable 82 of the earphone 8 into a slit 31 formed in the pad portion 3.
Figure 6:
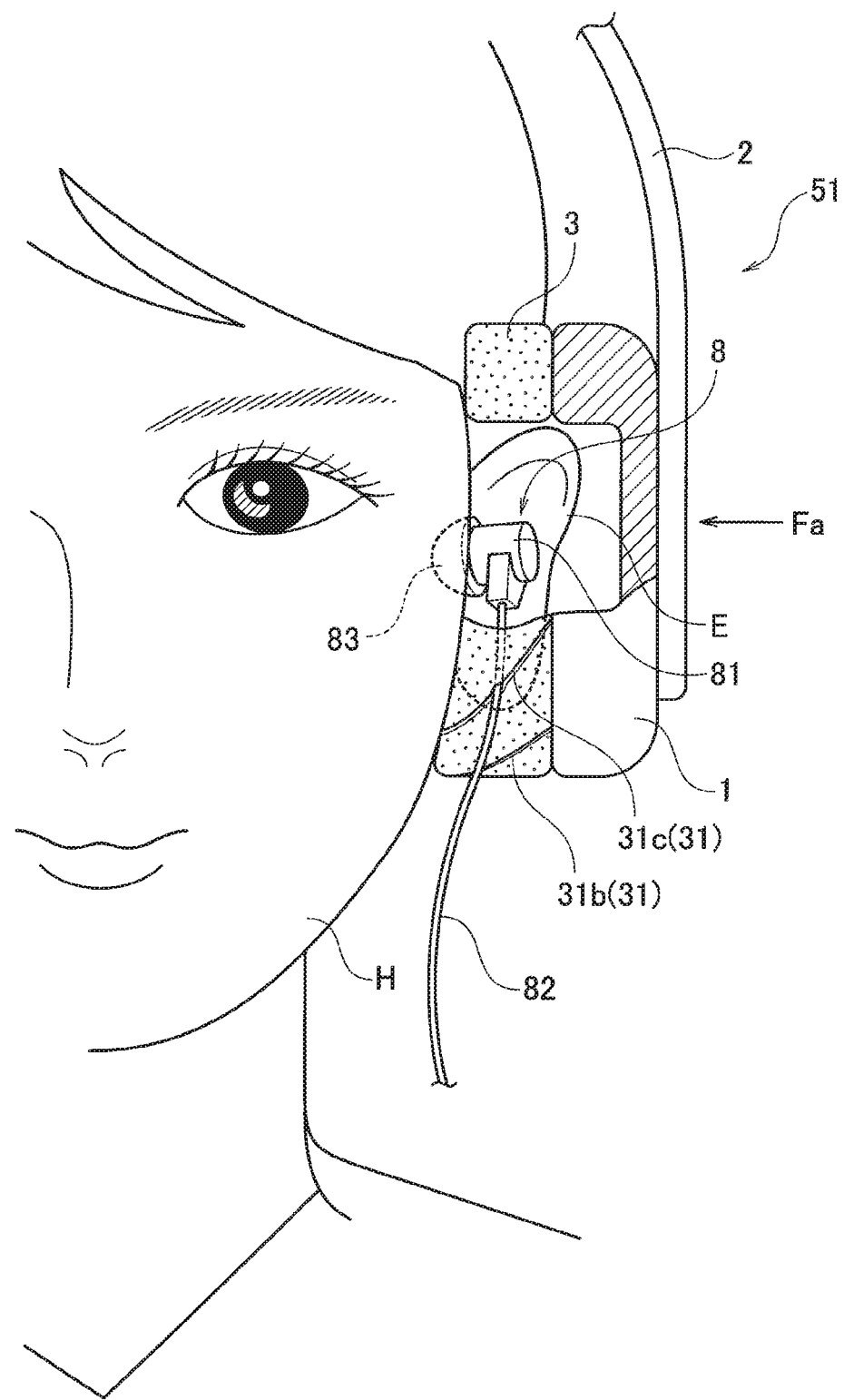
FIG. 6 is a partially cross-sectional front view illustrating a state of putting the earmuffs on the head H with the earphone 8 fitted in the outer ear.

FIG. 1 is a perspective view showing the earmuffs 51 put on the head H while an earphone 8 having a cable 82 is fitted in the outer ear E of the user (refer to FIG. 5 and FIG. 6). The forward, rearward, leftward, rightward, upward, and downward directions in the following explanations are defined by the respective arrows indicated in FIG. 1.

The earmuffs 51 include a pair of right and left body portions 1, a band portion 2 connecting the paired body portions 1 to each other, and pad portions 3 attached to the respective body portions 1.

FIG. 1 illustrates only the left body portion 1. FIG. 1 also illustrates a state in which the wired canalphone 8 is fitted into the outer ear E of the user (refer to FIG. 6), while the earmuffs 51 are put over the head H to cover the earphone 8 fitted in the outer ear E.

As shown in FIG. 5, the earphone 8 includes a body portion 81, an earpiece 83 attached to the tip of the body portion 81, and a cable 82 extending from the body portion 81.

Figure 2:
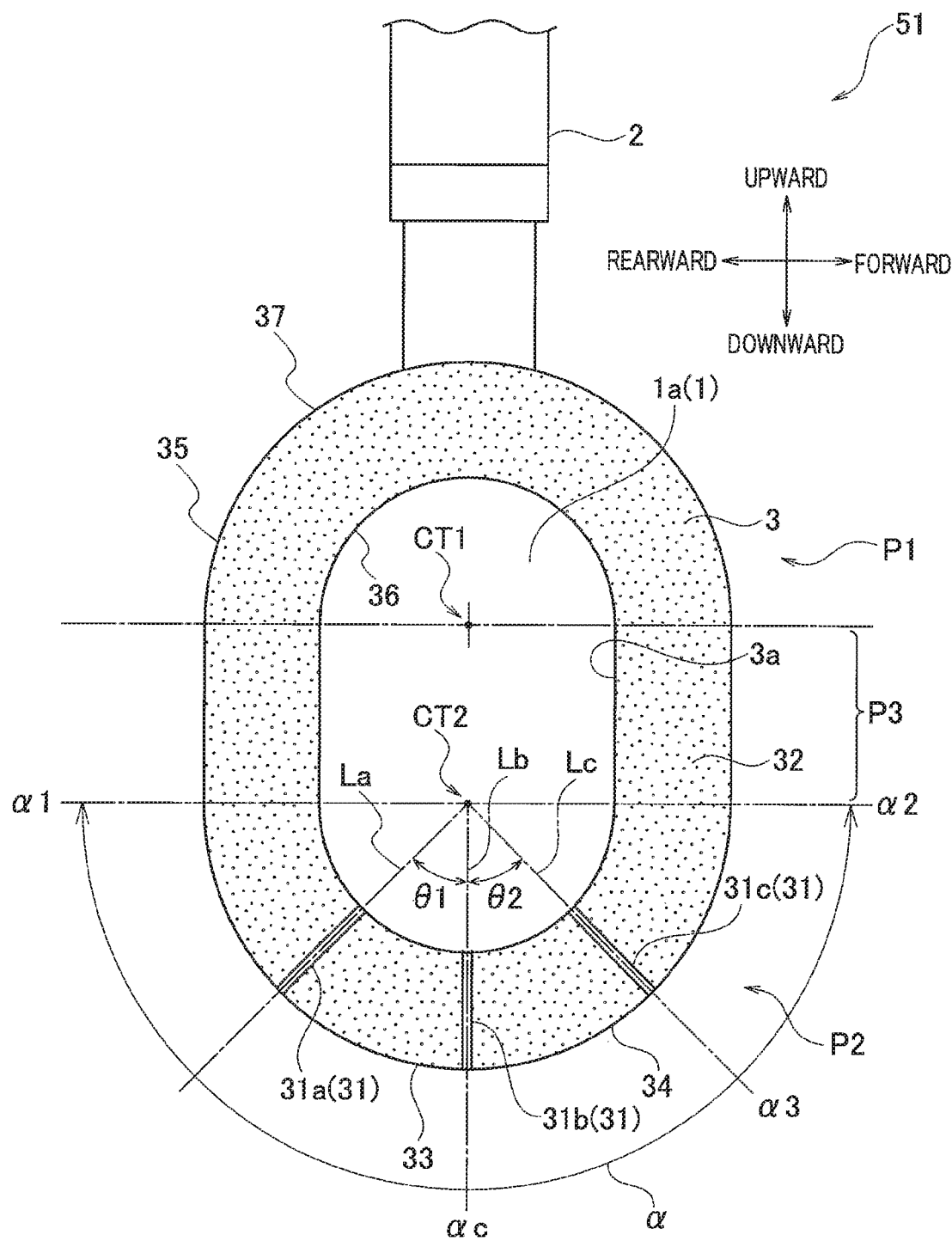
FIG. 2 is a plan view showing a body portion 1 of the earmuff 51 provided with a pad portion 3.

The cable 82 of the earphone 8 is led out of the pad portion 3 through a slit 31 formed in the pad portion 3, as shown in FIG. 2. The slits 31 are described in detail below.

The pad portion 3 includes a cushion member of a sponge body formed of chloroprene rubber, and having compression elasticity so as to be soft to the contact with the skin of the user, as in the case of conventional pad portions.

The pad portion 3 may be formed such that the cushion part is covered with a resin sheet, for example.

Figure 3:
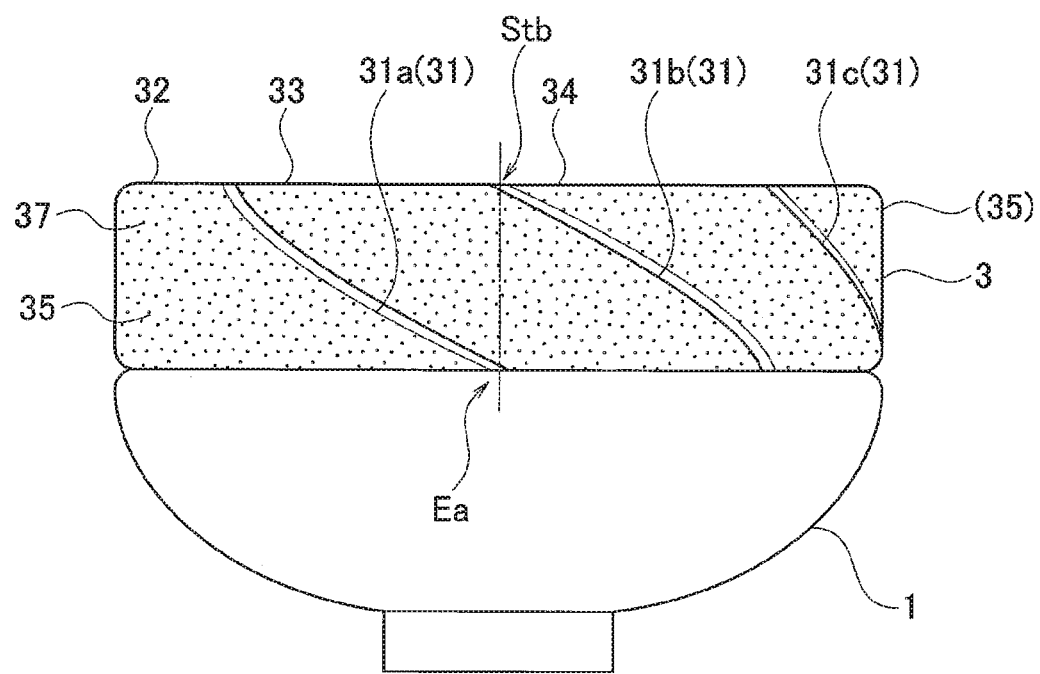
FIG. 3 is a bottom view showing the body portion 1 of the earmuff 51 provided with the pad portion 3.

FIG. 2 is a plan view showing the body portion 1 of the earmuff 51 provided with the pad portion 3, as viewed from the head H side with the earmuff 51 put on. FIG. 3 is a bottom view showing the body portion 1 provided with the pad portion 3.

The body portion 1 and the pad portion 3 have an oblong shape elongated in the vertical direction. In particular, as shown in FIG. 2, the body portion 1 and the pad portion 3 each include an upper part P1 and a lower part P2 having a semicircular shape defined about a position CT1 and a position CT2 vertically separated from each other, and an intermediate part P3 connecting the upper part P1 and the lower part P2 together.

The pad portion 3 is provided with a plurality of radiated slits 31, including slits 31a, 31b, and 31c, extending in the radial direction in the lower part P2.

The slit 31b is arranged along a radial line Lb passing through the position CT2 to extend immediately downward in the vertical direction on the surface of the pad portion 3.

The slit 31a is arranged along a radial line La inclined rearward to the slit 31b at a predetermined angle of θ1 on the surface of the pad portion 3.

The slit 31c is arranged along a radial line Lc inclined forward to the slit 31b at a predetermined angle of θ2 on the surface of the pad portion 3.

The respective predetermined angles θ1 and θ2 can be optionally determined, and may be 30 or 45 degrees, for example.

The predetermined angles θ1 and θ2 may be equal to or different from each other.

All of the slits 31 may be arranged on either the rear side or the front side of the radial line Lb passing through the position CT2 to extend immediately downward in the vertical direction on the surface of the pad portion 3, or one of the slits 31 may be arranged on either the rear side or the front side of the radial line Lb.

The respective slits 31 are open on the surface 32 to connect the inner circumferential surface 36 to the outer circumferential surface 37 of the pad portion 3. The surface 32 is a contact surface brought into contact with the head H when the earmuffs 51 are put on.

The pad portion 3 includes pad units 33, 34, and 35.

The pad unit 33 is a section between the slit 31a and the slit 31b. The pad unit 34 is a section between the slit 31b and the slit 31c. The pad unit 35 is a section defining the slit 31a together with the pad unit 33 opposed to and separated from each other, and defining the slit 31c together with the pad unit 34 opposed to and separated from each other.

The slits 31a to 31c open on the surface 32 of the pad portion 3 extend toward the body portion 1 obliquely in the same circumferential direction about the position CT2 shown in FIG. 2.

For example, as shown in FIG. 3, the slits 31a to 31c are gradually shifted from the surface 32 toward the body portion 1 counterclockwise in the circumferential direction about the position CT2. The shifted degree is set such that the deepest position Ea of one slit 31a on the body portion 1 side substantially conforms to the opening position Stb of the adjacent slit 31b on the surface 32.

Figure 4:
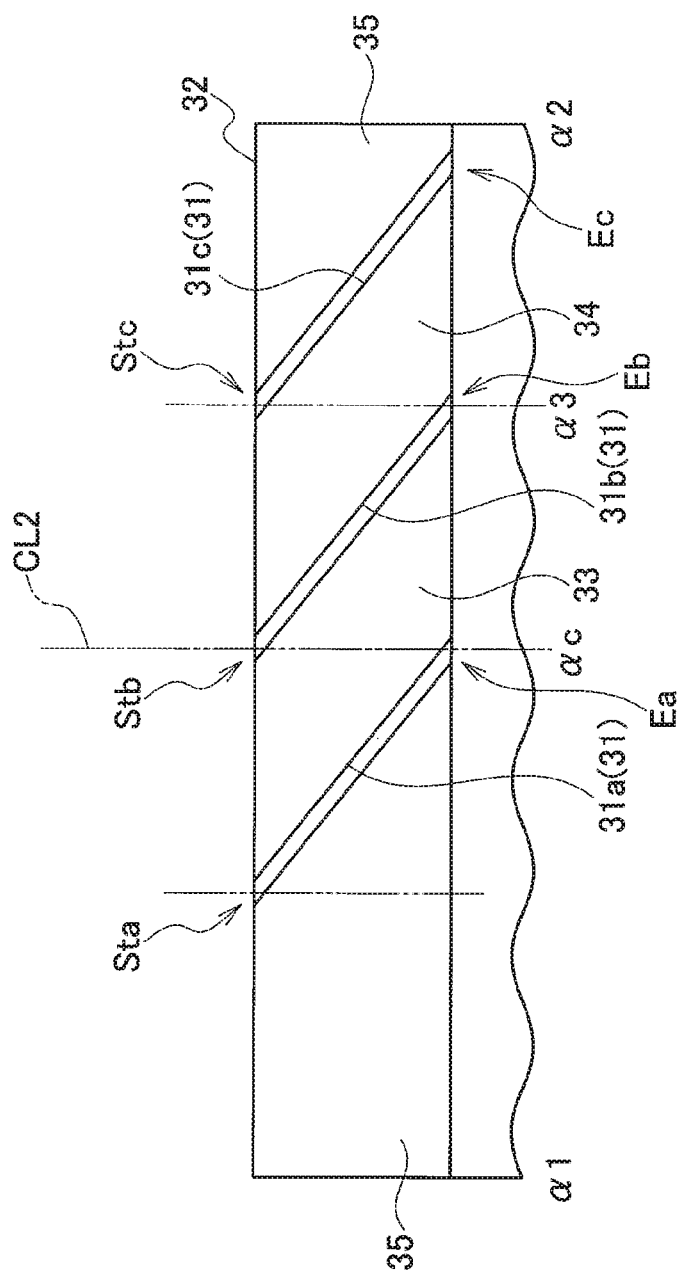
FIG. 4 is a partial developed view of the pad portion 3.

FIG. 4 is a developed plan view showing the lower part P2 of the pad portion 3 developed in a range α from an angular position α1 to an angular position α2 in the circumferential direction, as shown in FIG. 2.

The slit 31a shown in the developed plan view of FIG. 4 is inclined to an axial line CL2 passing through the position CT2 and extends straight from the opening position Sta to the deepest position Ea.

The deepest position Ea of the slit 31a conforms to an angular position ac in the middle of the range α. The angular position ac also conforms to the opening position Stb of the slit 31b adjacent to the slit 31a. An angular position α3 at the deepest position Eb of the slit 31b conforms to the opening position Stc of the slit 31c adjacent to the slit 31b.

FIG. 5 is a perspective view showing the body portion 1 provided with the pad portion 3 having the slits 31a to 31, and illustrating a process of inserting the cable 82 of the earphone 8 fitted in the outer ear E into one slit (31b) optionally chosen. This process may be performed before fitting the earphone 8 into the outer ear E, or may be performed before or after putting the earmuffs 51 on the head H after fitting the earphone 8 into the outer ear E.

FIG. 5 illustrates the case in which the user inserts the cable 82 into the slit 31b, and further moves the cable 82 forward in the extending direction of the slit 31b, as indicated by the arrow DRa.

The specific steps are illustrated in detail below.

The user first inserts the earpiece 83 into the ear canal to place the body portion 81 in the concha so as to fit the earphone 8 in the outer ear E with the cable 82 substantially hanging downward.

The user then sets the earmuffs 51 on the head H so as to allow the outer ears E to be located in the holes 3a of the pad portions 3. Since the cable 82 is still interposed between the pad portion 3 and the head H in this state, the user picks up the cable 82 with the fingers to move the cable 82 forward or rearward, as indicated by the arrow DRb, while slightly pressing the pad portion 3 toward the body portion 1.

While the user is moving and pushing the cable 82 against the pad portion 3, the cable 82 reaches any one of the opening positions Sta to Stc of the slits 31a to 31c to enter the corresponding slit, as indicated by the arrow DRa. FIG. 5 illustrates the case in which the cable 82 enters the slit 31b.

A width of the respective slits 31a to 31c is set to be substantially the same as or slightly smaller than the outer diameter of the cable 82. Each pad portion 3 is pressed and pressurized against the head H with the earmuffs 51 put on, due to pressure force Fa derived from elastic repulsive force of the band portion 2 shown in FIG. 6. The cable 82 inserted into the slit 31b is thus held and kept between the pad unit 33 and the pad unit 34 defining the slit 31b.

FIG. 6 is a partially cross-sectional front view showing the state of fitting the earphone 8 in the outer ear E with the earmuffs 51 put on the head H.

FIG. 6 illustrates that the cable 82 extending from the body portion 81 of the earphone 8 is led out of the pad portion 3 downward at a position in the middle of the slit 31c.

As described above, the body portion 1 and the pad portion 3 are pressed against the head H with the earmuffs 51 put on due to the pressure force Fa applied from the band portion 2.

Since the pad portion 3 is pressurized in the thickness direction, the pressurized and inclined slits 31a to 31c are thus in a substantially closed state.

In particular, the inclined surfaces between the pad unit 35 and the pad unit 33, the inclined surfaces between the pad unit 33 and the pad unit 34, and the inclined surfaces between the pad unit 34 and the pad unit 35, defining the slit 31a, the slit 31b, and the slit 31c, respectively, are pressurized in the thickness direction so as to be brought into contact with each other.

The cable 82 is thus held and kept at a position in the middle of the slit 31c with substantially no gap between the pad unit 34 and the pad unit 35 on both sides of the slit 31c.

The earmuffs 51 having the slits can ensure the sound insulating properties, since the gaps of the respective slits 31 are substantially closed when being put on the head H. The earmuffs 51 can prevent outside noise from reaching the ears without disturbing hearing of the sound playback from the earphone 8, and can practically prevent leakage of the sound playback from the earphone 8 to the outside.

The user thus can hear the sound playback from the earphone 8 reliably when fitting the earphone 8 having the cable 82 in the outer ear E together with the earmuffs 51 put on the head H.

As described above, the slits 31a to 31c are arranged such that the deepest position Ea of the slit 31a conforms to the opening position Stb of the adjacent slit 31b in the circumferential direction in the lower part P2, for example. The led-out position of the cable 82 in the circumferential direction can be defined at any position in the range between the opening position Sta of the slit 31a and the deepest position Ec of the slit 31c. The led-out direction of the cable 82 thus can be freely changed in the circumferential direction within the arc-like continuous region in which the respective slits 31 are provided. This facilitates the handling and improves the easiness of wearing when using both the earphone 8 and the earmuffs 51 together.

The set of slits 31 is only required to include paired slits adjacent to each other in which the deepest position of one of the slits conforms to the opening position of the other slit in the circumferential direction.

The structure including such paired slits adjacent to each other can allow the led-out direction of the cable 82 to be freely changed in the circumferential direction within the arc-like continuous region in which the paired slits are provided.

The paired slits may partly overlap with each other in the circumferential direction. In particular, one of the slits and the other slit can be arranged such that the opening position of the other slit is shifted from the deepest position toward the opening position of the one slit.

This arrangement can still allow the led-out direction of the cable 82 to be freely changed in the circumferential direction within the arc-like continuous region in which the paired slits are provided.

Figure 7:
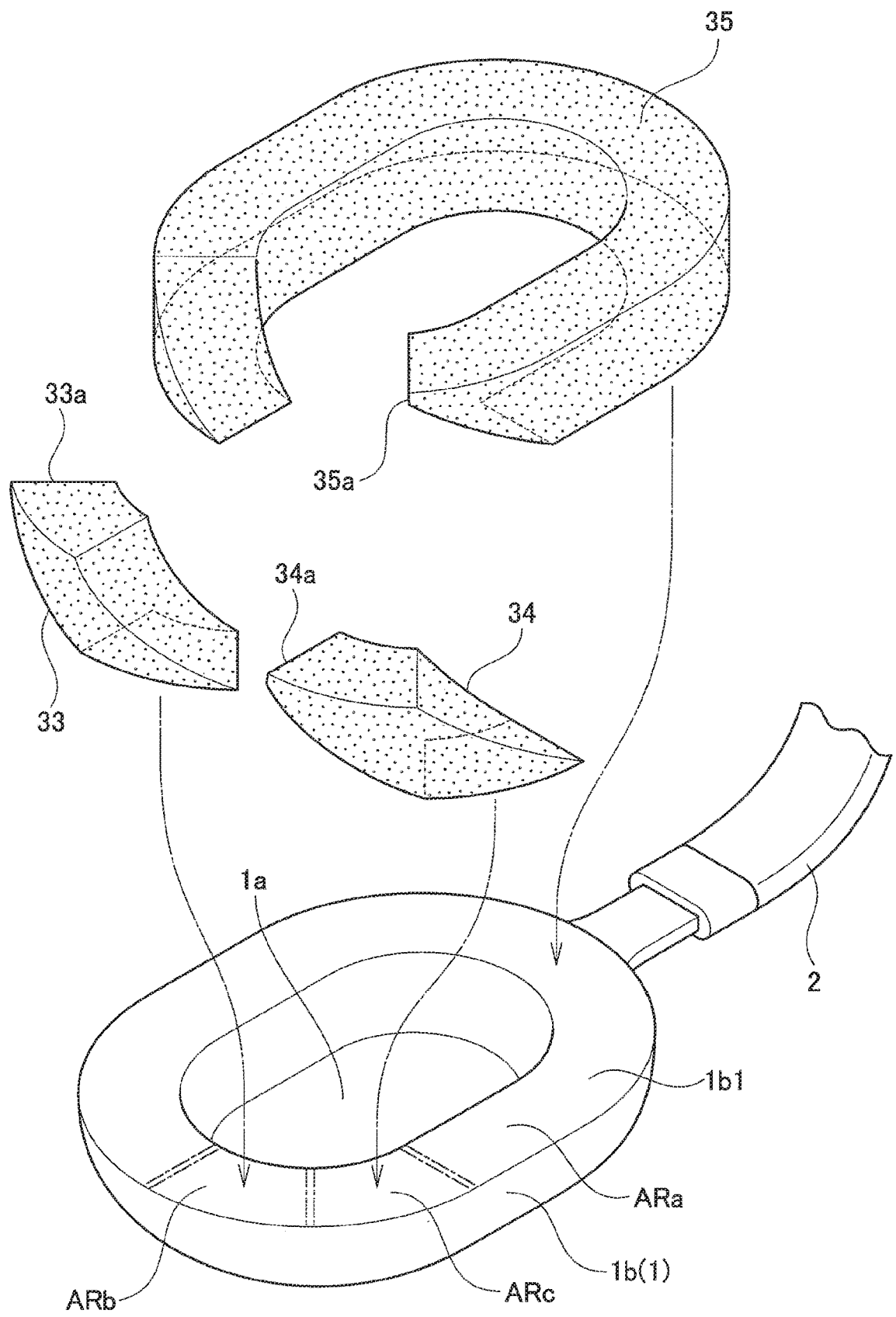
FIG. 7 is an exploded perspective view illustrating a method of producing the pad portion 3.

FIG. 7 is an exploded perspective view illustrating a method of producing the pad portion 3.

The body portion 1 includes, for example, a bottom portion 1a and a circular wall portion 1b extending upward along the circumference of the bottom portion 1a. The positions of the slits 31a to 31c to be formed on a pad attachment surface 1b1 as a top surface of the wall portion 1b, as shown in FIG. 7, are shifted from the positions of the slits 31a to 31c in the circumferential direction described above with reference to FIG. 2.

The pad portion 3, when having three slits 31, includes three pad units 33, 34, and 35 attached by bonding, for example, to three regions ARb, ARc, and ARa arranged with slight gaps interposed therebetween on the pad attachment surface 1b1 of the wall portion 1b so as to define the respective slits 31.

The pad units 33, 34, and 35 are provided with rounded portions 33a, 34a, and 35a at the respective tips each having an acute angle at the opening on the surface 32 side. The rounded portions 33a, 34a, and 35a avoid damage to the tip portions of the pad units 33, 34, and 35, and also each serve as a guide when the user inserts the cable 82 into any one of the slits 31.

It should be understood that the present disclosure is not intended to be limited to the above example, and various modifications can be made within the scope of the present disclosure.

The number, the gaps, and the shifted direction of the slits 31 may be determined as appropriate.

The shape of the body portion 1 and the pad portion 3 is not limited to the oblong shape, and may be any of a true circle, an oval, or a rectangle.

The earmuffs 51 may include the band portion 2 not to be put over the top of the head but to be put across the back of the neck.

What is claimed is:

1. An earmuff comprising:
a body portion; and
a circular pad portion having a contact surface brought into contact with a head of a user during use, the circular pad portion being attached to the body portion and including a cushion member which has a thickness extending from the contact surface to the deepest position attached to the body portion;
the pad portion being provided with at least one slit connecting a circular inner circumferential surface and a circular outer circumferential surface and open on the contact surface, the slit cut into the pad portion and formed from the contact surface to the deepest portion so as to be gradually shifted toward the body portion in a circumferential direction.

2. The earmuff according to claim 1, wherein:
the pad portion includes a plurality of slits each corresponding to the at least one slit; and
the plural slits include paired slits adjacent to each other in which a deepest position of one of the slits conforms to an opening position of another slit in a circumferential direction.

3. The earmuff according to claim 1 comprising a pair of earmuffs configured as an earmuff pair, wherein:
the earmuff pair comprises the body portion for each of the right and left ears of the user, and a band portion connecting the paired body portions; and
the body portions are pressed against the head due to elastic repulsive force of the band portion when put on the head, thereby causing gaps of the slits included in the pad portion to be closed.

4. An earmuff comprising:
a body portion;
a circular pad portion attached to the body portion and having a contact surface brought into contact with a head of a user during use; and
the pad portion being provided with at least one slit connecting an inner circumferential surface and an outer circumferential surface and open on the contact surface, the slit being cut into the pad portion so as to be gradually shifted toward the body portion in a circumferential direction,
wherein the pad portion includes a plurality of slits each corresponding to the at least one slit,
and wherein the plural slits include paired slits adjacent to each other in which a deepest position of one of the slits conforms to an opening position of another slit in a circumferential direction.

5. An earmuff comprising:
a body portion;
a circular pad portion attached to the body portion and having a contact surface brought into contact with a head of a user during use;
the pad portion being provided with at least one slit connecting an inner circumferential surface and an outer circumferential surface and open on the contact surface, the slit being cut into the pad portion so as to be gradually shifted toward the body portion in a circumferential direction; and
the earmuffs configured as an earmuff pair,
wherein the earmuff pair comprises the body portion for each of the right and left ears of the user, and a band portion connecting the paired body portions,
and wherein the body portions are pressed against the head due to elastic repulsive force of the band portion when put on the head, thereby causing gaps of the slits included in the pad portion to be closed.

* * * * *